United States Patent [19]
Bayston et al.

[11] Patent Number: 6,140,516
[45] Date of Patent: Oct. 31, 2000

[54] PROCESS FOR THE PREPARATION OF TRANS-3-ALKYLOXY-4-HYDROXYTETRAHYDROFURAN

[75] Inventors: Daniel John Bayston, Oxfordshire; Sharon Casson, Oxon; James Matthew Lovell; Ronald Michael Scott, both of Oxfordshire, all of United Kingdom

[73] Assignee: Eastman Chemical Company, Kingsport, Tenn.

[21] Appl. No.: 09/465,189

[22] Filed: Dec. 15, 1999

[51] Int. Cl.[7] .......................... C07D 309/10; C12P 17/04
[52] U.S. Cl. ........................ 549/476; 549/478; 435/126
[58] Field of Search ........................ 549/476, 478; 435/126

[56] References Cited

U.S. PATENT DOCUMENTS 4,169,152  9/1979  LeMaistre et al. ................ 549/476

FOREIGN PATENT DOCUMENTS 743 308 A2  11/1996  European Pat. Off. .

OTHER PUBLICATIONS

Liboska, Collect. Czech. Commun., vol. 61, p. S72–S75, 1996.
Liebigs Annalen Der Chemie, vol. 95, p. 138 and 139, 1955.
Hawkins et al, J. Chem. Soc., p. 248–256, 1959.
R. Seemayer et al, J. Chem. Soc. Perkin Trans. 1, 2359–60 (1990).
Wei Wang et al, Bioorg. Med. Chem. Letters, vol. 7, No. 20, 2567–72 (1997).
K. Tatani et al, Tetrahedron Letters, 39, 5065–68 (1998).
A. Borner et al, J. Org. Chem., 58, 6814–17 (1993).
H. Altenbach et al, Tetrahedron:Asymmetry, vol. 4, No. 10, 2155–58 (1993).
P. Barili et al; Tetrahedron, vol. 49, No. 28, 6263–76 (1993).
A Terfort, Synthesis, 951–953 (Oct., 1992).
Barriere et al, Tetrahedron Letters, vol. 26, No. 26, 3121–24 (1985).
H. Dulphy et al, Tetrahedron, vol. 52, No. 25, 8517–24 (1996).
W. Jackson et al, Aust. J. Chem. 35, 2069–75 (1982).
G. H. Posner et al, J. Am. Chem. Soc. 99:25, 8208–14 (1977).
J. Otera et al, Tetrahedron, vol. 47, No. 36, 7625–34 (1991).
N. Iranpoor et al, Tetrahedron Letters, vol. 31, No. 5 735–38 (1990).
P. Chini et al, Synlett, 673–76 (1992).
G. Guanti et al, Tetrahedron Letters. vol. 27, No. 38, 4639–42 (1986).
D. R. Deardoff et al, Tetrahedron Letters., vol. 27, No. 11, 1255–56 (1986).
E. Schoffers et al, Tetrahedron, vol. 52, No. 11, 3769–3826 (1996).
S. Roberts, J. Chem. Soc. Perkin Trans. 1, 1–21 (1998).

*Primary Examiner*—Bernard Dentz
*Attorney, Agent, or Firm*—Michael J. Blake; Harry J. Gwinnell

[57] ABSTRACT

Disclosed is a process for preparing novel trans-3-alkyloxy-4-hydroxytetrahydrofurans including racemic and substantially enantiomerically pure (3S,4S)-trans-3-alk(en)yloxy-4-hydroxytetrahydrofurans and (3R,4R)-trans-3-alk(en)yloxy-4-acyloxytetrahydrofurans. The disclosed process comprises the steps of reacting 3,4-epoxytetrahydrofuran with an alcohol under Lewis acid catalysis to obtain a racemic trans-3-alk(en)yloxy-4-hydroxytetrahydrofuran; contacting the trans-3-alk(en)yloxy-4-hydroxytetrahydrofuran with an acyl donor in the presence of a hydrolase enzyme to produce a mixture of a substantially enantiomerically pure (3S,4S)-trans-3-alk(en)yloxy-4-hydroxytetrahydrofuran and a substantially enantiomerically pure (3R,4R)-trans-3-alk(en)yloxy-4-acyloxytetrahydrofuran; and separating the components of the mixture by partitioning between water and a solvent immiscible with water.

9 Claims, No Drawings

PROCESS FOR THE PREPARATION OF TRANS-3-ALKYLOXY-4-HYDROXYTETRAHYDROFURAN

INTRODUCTION

This invention pertains to a process for preparing trans-3-alkyloxy-4-hydroxytetrahydrofurans including racemic and substantially enantiomerically pure (3S,4S)-trans-3-alk(en)yloxy-4-hydroxytetrahydrofurans and (3R,4R)-trans-3-alk(en)yloxy-4-acyloxytetrahydrofurans. More specifically, this invention pertains to a 3-step process for the preparation of trans-3-alk(en)yloxy-4-hydroxytetrahydrofurans wherein 3,4-epoxytetrahydrofuran is reacted with an alcohol under Lewis acid catalysis to obtain a racemic trans-3-alk(en)yloxy-4-hydroxytetrahydrofuran; the trans-3-alk(en)yloxy-4-hydroxytetrahydrofuran is contacted with an acyl donor in the presence of a hydrolase enzyme to produce a mixture of a substantially enantiomerically pure (3S,4S)-trans-3-alk(en)yloxy-4-hydroxytetrahydrofuran and a substantially enantiomerically pure (3R,4R)-trans-3-alk(en)yloxy-4-acyloxytetrahydrofuran; and the components of the mixture are separated by partitioning between water and a solvent immiscible with water. The present invention also includes certain of the individual process steps and intermediate compounds.

Oxygenated tetrahydrofuran derivatives are an important class of organic compounds and often are found in physiologically active compounds. See, for example, T. S. Mansour, Bioorg. Med. Chem. Lett., 7, 2567 (1997); A. Matsuda Tetrahedron Lett., 39, 5065 (1998) and European Patent Application EP 743308 A2. Enantiomerically enriched substituted or unsubstituted 3,4-dihydroxytetrahydrofuran derivatives have been prepared by various methods. See, for example, A. Borner, J. Org. Chem., 58, 6814 (1993); H. Alfenbach, Tetrahedron: Asymmetry, 4, 2155 (1993); E. Mastrorilli, Tetrahedron, 49, 6263 (1993); A. Terfort, Synthesis, 951 (1992); Barton and Gero, Tetrahedron Lett., 26, 3121 (1985) and J. Gras, Tetrahedron, 52, 8517 (1996).

Typically, enantiomerically enriched 3,4-dihydroxytetrahydrofuran derivatives have been synthesized by hydride reduction of tartaric acid to give a tetraol, followed by subsequent cyclisation as described in W. Jackson and C. Lovel, Aust. J. Chem. 35, 2069 (1982) and A. Terfort, Synthesis, 951 (1992). Handling of the intermediate polyalcohol is known to be difficult due to its extreme water solubility, and this is especially problematic when the polyalcohol must be separated from salts generated from the hydride reagent. Other procedures that would avoid this type of compound would be much preferred from a process point of view. The process described herein is one such procedure.

The opening of epoxides with alcohols in the presence of an acid catalyst is well known as is exemplified by G. H. Posner, J. Am. Chem. Soc., 99, 8208 (1977); J. Otera, Tetrahedron, 47, 7625 (1991); N. Iranpoor, Tetrahedron Lett., 31, 735 (1990) and P. Crotti, Synlett, 673 (1992). The use of sulphuric acid as a catalyst in the alcoholysis of 3,4-epoxytetrahydrofuran is described in E. G. E. Hawkins, J. Chem. Soc., 251 (1959). The opening of epoxides with alcohols often uses strong acids such as sulphuric acid in refluxing alcohol which, in the case of 3,4-epoxytetrahydrofuran, leads to low yields of adducts due to polymerization and decomposition. Alternative methods also tend to require the use of high temperature and expensive or unstable catalysts.

The use of enzymes to resolve racemic alcohols is a well-known reaction described, for example, in G. Guanti, Tetrahedron Lett. 27, 4639 (1986); D. R. Deardorff, Tetrahedron Lett., 27, 1255 (1986); C. R. Johnson, Tetrahedron, 52, 3769 (1996) and S. Roberts, J. Chem. Soc. Perkin Trans. I, 1 (1999). Enzyme resolution of both cis and trans-3-alkoxy-4-acetoxytetrahydrofuran has been reported in M. P. Schneider, J. Chem. Soc. Perkin Trans., I 2359 (1990). The resolution described by Schneider uses an esterhydrolase (SAM-II from Pseudomonas sp.) to hydrolyze the acetoxy functionality to an alcohol. A particular disadvantage of that procedure is that it results in an imperfect resolution such that only one of the components of the starting material or product can be obtained with a high enantiomeric excess (>98% enantiomeric excess—ee). The other component necessarily is obtained with a relatively low enantiomeric excess (~80% ee).

BRIEF SUMMARY OF THE INVENTION

We have developed a process for the preparation of both racemic trans-3-alk(en)yloxy-4-hydroxytetrahydrofuran (I) and substantially enantiomerically pure (3S,4S)-trans-3-alk(en)yloxy-4-hydroxytetrahydrofuran (Ia) and (3R,4R)-trans-3-alk(en)yloxy-4-acyloxytetrahydrofuran (II) beginning with 3,4-epoxytetrahydrofuran which is available by epoxidation of 2,5-dihydrofuran. Our novel process, therefore, comprises the steps of:

(1) contacting 3,4-epoxytetrahydrofuran with an alcohol having the formula $R^1$—OH in the presence of an acid catalyst in an inert solvent to obtain a trans-3-alk(en)yloxy-4-hydroxytetrahydrofuran (I) of the formula:

(2) contacting trans-3-alk(en)yloxy-4-hydroxytetrahydrofuran of formula (I) with a hydrolase enzyme and an acyl donor in the presence of an aprotic solvent to obtain a mixture of a substantially enantiomerically pure (3S,4S)-trans-3-alk(en)yloxy-4-hydroxytetrahydrofuran having formula (Ia) and a substantially enantiomerically pure (3R,4R)-trans-3-alk(en)yloxy-4-acyloxytetrahydrofuran of formula (II):

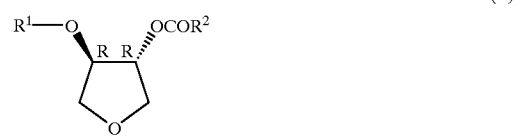

(3) separating (Ia) and (II) from the mixture obtained in step (2) by partitioning the mixture between water and a water-immiscible solvent to obtain the (3S,4S)-trans-3-alk(en)yloxy-4-hydroxytetrahydrofuran (Ia) in the aqueous phase and the (3R,4R)-trans-3-alk(en)yloxy-4-acyloxytetrahydrofuran (II) in the water-immiscible solvent.

wherein R¹ is an alkyl, alkenyl or aryl radical and R² is an alkyl radical.

The present invention also includes the novel compounds produced in the above-described process, i.e., the racemic trans-3-alk(en)yloxy-4-hydroxytetrahydrofurans (I), the substantially enantiomerically pure (3S,4S)-trans-3-alk(en)yloxy-4-hydroxy-tetrahydrofuran (Ia) and the substantially enantiomerically pure (3R,4R)-trans-3-alk(en)yloxy-4-acyloxytetrahydrofurans (II).

One advantage of the present invention is the extremely mild reaction conditions (e.g., room temperature) for the nucleophilic opening of 3,4-epoxytetrahydrofuran with an alcohol. Furthermore, the economical and readily available boron triflouride may be used as the catalyst rather than the more expensive catalysts mentioned above. The reaction time for the esterification of the alcohol to the carboxylate ester depends on the amount and activity of the enzyme used, but is typically about 24 hours. The enantioselectivity of the enzymatic reaction is near perfect such that both starting material and product from the enzyme resolution may be obtained with >98% enantiomeric excess.

DETAILED DESCRIPTION

In step (1) of the process, 3,4-epoxytetrahydrofuran is reacted with an alcohol in the presence of an acid catalyst in an inert solvent to produce racemic trans-3-alkyloxy-4-hydroxytetrahydrofuran (I). The alcohol may be selected from a variety of alkanols and alkenols containing, for example, up to about 8 carbon atoms. Examples of such alcohols are those having the general formula $R^1$—OH wherein $R^1$ may be an unsubstituted or substituted $C_1$–$C_8$ alkyl; arylalkyl such as benzyl or phenethyl; carbocyclic aryl such as phenyl or phenyl substituted, for example with alkyl, alkoxy and/or halogen; or $C_2$–$C_6$ alkenyl such as allyl. Alcohol $R^1$—OH preferably is allyl alcohol. The acid catalyst preferably is selected from sulphuric acid, boron trifluoride, an alkali or alkaline earth metal tetrafluoroborate, an alkali or alkaline earth metal trifluoromethanesulphonate or an alkali or alkaline earth metal perchlorate, e.g., magnesium perchlorate. Boron trifluoride is the most preferred acid catalyst.

The inert solvent employed in the first step preferably is an ether, e.g., a dialkyl ether containing 2 to 8 carbon atoms or tetrahydrofuran; a hydrocarbon, e.g., an aliphatic hydrocarbon containing 6 to 12 carbon atoms, a cycloaliphatic hydrocarbon containing 5 to 7 carbon atoms or an aromatic hydrocarbon containing 6 to about 12 carbon atoms such as benzene and alkyl-substituted benzene, e.g., toluene, the xylenes and diisopropylbenzene; an aliphatic nitrile containing 2 to 8 carbon atoms, e.g., acetonitrile and isobutyrnitrile; or a chlorinated hydrocarbon, e.g., chlorinated aliphatic hydrocarbons containing up to 3 carbon atoms and chlorinated aromatic hydrocarbons such as mono-, di- and tri-chlorobenzene. The most preferred inert solvents are dichloromethane and isobutyronitrile. The first step may be carried out at a temperature in the range of about 0° C. up to the boiling point of the solvent, preferably at a temperature of about 20 to 100° C. The mole ratio of 3,4-epoxytetrahydrofuran:alcohol normally may be in the range of about 1:1 to 1:10 but preferably is about 1:5. Trans-3-alk(en)yloxy-4-hydroxytetrahydrofuran (I) produced in step (1) may be isolated using conventional procedures, e.g., by standard extraction techniques known in the art followed by distillation.

The second step of the process comprises contacting trans-3-alk(en)yloxy-4-hydroxytetrahydrofuran (I) obtained from the first step with an enzyme esterase and an acyl donor in the presence of an inert (nonreactive) aprotic solvent to obtain a mixture of substantially enantiomerically pure (3S,4S)-trans-3-alk(en)yloxy-4-hydroxytetrahydrofuran of formula (Ia) and (3R,4R)-trans-3-alk(en)yloxy-4-acyloxytetrahydrofuran of formula (II). The enzyme may be either a lipase or an esterase such as those available under the tradenames Novozym 435, Amano PS, Amano I or Amano II. Novozym 435 is the most preferred enzyme. The weight ratio of enzyme:trans-3-alk(en)yloxy-4-hydroxytetrahydrofuran will depend on the purity and activity of the enzyme, and will normally be about 0.01:1 to 1:1 but is preferably 0.05 to 0.2:1. The acyl donor or acylating agents may be an ester or anhydride of an aliphatic carboxylic acid (alkanoic acid) containing up to a total of about 12 carbon atoms. Examples of the esters include alk(en)yl carboxylate esters having the general formula

$R^2$—COO—$R^3$ wherein $R^2$ is alkyl, e.g., alkyl containing from 1 to 4 carbon atoms, especially methyl, and $R^3$ is alkyl containing from 1 to 6 carbon atoms or alkenyl containing 2 to 4 carbon atoms. Specific examples of alk(en)yl carboxylate esters include ethyl acetate, isopropyl acetate and the most preferred vinyl acetate. The carboxylic acid anhydrides may be cyclic or acyclic and preferably contain a total of 4 to 10 carbon atoms. The mole ratio of acyl donor:trans-3-alkyloxy-4-hydroxytetrahydrofuran may be in the range of about 0.5:1 to 5:1 but preferably is about 0.8:1 to 3:1.

The solvent used in step (2) may be an ether, e.g., a dialkyl ether containing 2 to 8 carbon atoms or tetrahydrofuran; a hydrocarbon, e.g., an aliphatic hydrocarbon containing 6 to 12 carbon atoms, a cycloaliphatic hydrocarbon containing 5 to 7 carbon atoms or an aromatic hydrocarbon containing 6 to about 12 carbon atoms such as benzene and alkyl-substituted benzene, e.g., toluene, the xylenes and diisopropylbenzene; or an alkyl carboxylate ester, e.g., the alkyl carboxylate ester described in the preceding paragraph; or a mixture of any 2 or more thereof. The solvent for step (2) preferably is cyclohexane. The second step may be carried out at a temperature in the range of 20° C. up to the boiling point of the solvent, preferably at a temperature of about 20 to 80° C., most preferably 20 to 60° C.

In the third step of the process, the mixture of the (3S,4S)-trans-3-alk(en)yloxy-4-hydroxytetrahydrofuran of formula (Ia) and the (3R,4R)-trans-3-alk(en)yloxy-4-acyloxytetrahydrofuran of formula (II) produced in step (2) are separated by partitioning the mixture between water and a water-immiscible solvent to separate the mixture into its components. The water-immiscible solvent may be an ether, e.g., a dialkyl ether containing 2 to 8 carbon atoms or tetrahydrofuran; a hydrocarbon, e.g., an aliphatic hydrocarbon containing 6 to 12 carbon atoms, a cycloaliphatic hydrocarbon containing 5 to 7 carbon atoms or an aromatic hydrocarbon containing 6 to about 12 carbon atoms such as benzene and alkyl-substituted benzene, e.g., toluene, the xylenes and diisopropylbenzene; or an alkyl carboxylate ester, e.g., the alkyl carboxylate esters described above. The preferred water-immiscible solvents for the partitioning procedure of step (3) are hydrocarbons, most preferably cyclohexane.

In the partitioning or extraction procedure of step (3) a solution of the mixture produced in step (2) dissolved in the water-immiscible solvent (organic solution) is intimately contacted with water using known extraction procedures and equipment. The concentration of the step (2) mixture in the water-immiscible solvent typically is in the range of about 10 to 30 weight percent. The amount of water employed in the extraction may be about 0.25 to 5 volumes of water per volume of the organic solution. The temperature of the liquids involved in the partitioning of step (3) may be in the range of about 5 to 50° C. but normally is approximately ambient temperature.

At the end of the partitioning procedure, the water phase containing most of the (3S,4S)-trans-3-alk(en)yloxy-4-hydroxytetrahydrofuran (Ia) is separated from the water-immiscible phase which contains most of the (3R,4R)-trans-3-alkyloxy-4-acyloxytetrahydrofuran (II). Componds (Ia) and (II) may be isolated by distillation, typically under reduced pressure. Isolation of Compound (Ia) may be facilitated by extracting it from its solution in water into a lower boiling organic solvent such as a chlorinated hydrocarbon and then removing the organic solvent by distillation under reduced pressure.

EXAMPLES

The operation of the process and preparation of the novel compounds provided by our invention are further illustrated by the following examples. The identities of the products obtained were confirmed by nuclear magnetic resonance spectrometry, mass spectrometry and infrared spectrometry. The percentages specified in the examples are by weight unless otherwise specified.

Example 1

To a 10-L flask fitted with a double surface condenser, overhead stirrer and nitrogen inlet was added 3,4-epoxytetrahydrofuran (750 g, 8.71 mol), dichloromethane (3750 ml, 5 vol) and allyl alcohol (2530 g, 43.56 mol, 5 eq.). The solution was cooled to between 0° and 5° C. and boron trifluoride diethyletherate (61.8 g, 0.436 mol, 0.05 eq.) was added dropwise whilst maintaining the temperature below 10° C. After addition was complete the solution was allowed to warm to room temperature at which point the reaction slowly exothermed to reflux. After 3 hours $^1$H NMR analysis showed that no epoxide remained and the reaction was quenched with saturated aqueous sodium hydrogen carbonate solution (1500 mL, 2 vol). The phases were separated and the organic phase was washed with a further portion of saturated aqueous sodium hydrogen carbonate solution (1500 mL, 2 vol). The combined aqueous washes were extracted with $CH_2Cl_2$ (5×750 ml, 1 vol). After drying the organic phases over $MgSO_4$, filtering and concentrating in vacuo, the trans-3-allyloxy-4-hydroxytetrahydrofuran (I) was isolated by reduced pressure distillation (bp 94° C. @ 3 mbar) to give 1004.0 g (79.9% yield) of a clear colorless liquid.

Trans-3-Allyloxy-4-hydroxytetrahydrofuran (I) obtained from the first step as described above (250.0 g, 1.734 mol, 1 eq), cyclohexane (1000 ml, 4 vol), vinyl acetate (119.4 g, 128 mL, 1.387 mol, 0.8 eq) and NOVOZYM 435 (12.5 g, 5 wt %) were stirred at 50° C. under an atmosphere of $N_2$. GC analysis after 29 hours showed that the reaction was 50% complete and both the acetate produced and the unreacted alcohol had an ee of >98%. After cooling to room temperature the reaction mixture was filtered to remove the enzyme and the filter cake was washed with cyclohexane (2×125 mL, 0.5 vol).

The combined cyclohexane phases from step (2) above were washed with water (4×250 mL, 1 vol), dried over $MgSO_4$ and concentrated in vacuo. Distillation of the crude product under reduced pressure (bp 87° C. @ 3 mbar) gave (3R,4R)-trans-3-allyloxy-4-acetoxytetrahydrofuran (II) 114.0 g (70.6% yield, >98% ee). The combined aqueous washes were extracted with $CH_2Cl_2$ (4×50 mL, 0.2 vol) and then saturated with sodium chloride. The saturated aqueous washes were then extracted with $CH_2Cl_2$ (5×250 m, 1 vol) and the $CH_2Cl_2$ extracts dried over $MgSO_4$, filtered and concentrated in vacuo. Distillation of the crude alcohol under reduced pressure (bp 91° C. @ 1.5 mbar) afforded (3S,4S)-trans-3-allyloxy-4-hydroxytetrahydrofuran (Ia) (72.5 g, 58% yield, >98% ee).

The allyl group of (Ia) was cleaved by the action of 5% dry palladium on carbon (0.2 weight percent) in 10 volumes of refluxing ethanol. 3,4-Dihydroxytetrahydrofuran was obtained in 75% yield after distillation. Use of (Ia) with >98% ee gave (3S, 4S)-3,4-dihydroxytetrahydrofuran without loss of enantiomeric purity.

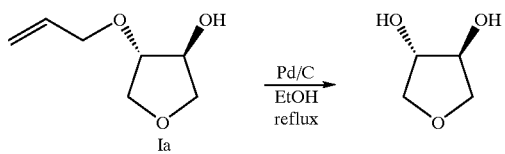

An analogous reaction to cleave the protecting groups of acetate (II) required the addition of an acid catalyst to completely remove the acetate group. The most suitable acid to use was found to be trifluoroacetic acid (0.1 eq) as it is easy to separate from the product.

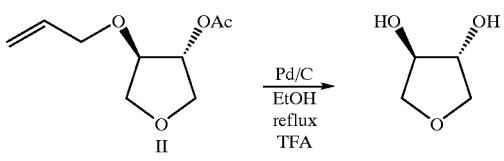

Starting with (II) with >98% ee (3R, 4R)-3,4-dihydroxytetrahydrofuran was isolated in 60% yield. No racemisation took place under these deprotection conditions. Other possible reagents which may be used to cleave the allyl group of (Ia) are those typical for the removal of an allyl group such as $(PPh_3)_3RhCl$ or $[Ir(COD)(Ph_2MeP)2]$ $PF_6$ wherein Ph is phenyl and Me is methyl. The above procedure utilizing palladium-on-carbon may be used to cleave the benzyl group from compounds (I) or (II) wherein $R^1$ is benzyl although the reaction would be run under an atmosphere of hydrogen.

Example 2

To a flask fitted with a condenser and nitrogen inlet was added 3,4-epoxytetrahydrofuran (20 g, 0.23 mol), isobutyronitrile (100 ml, 5 vol), benzyl alcohol (124 g, 1.15 mol, 5 eq.) and finally magnesium perchlorate (10.3 g, 0.046 mol, 0.2 eq). The solution was heated at 100° C. for 24 hours. After cooling to room temperature, the reaction was quenched with water (1000 mL). The phases were separated and the aqueous phase was extracted with ethyl acetate (3×400 mL). After drying the organic phases over $MgSO_4$, filtering and concentrating in vacuo, the trans-3-benzyloxy-4-hydroxytetrahydrofuran was isolated by column chromatography to give 29 g (66% yield) of a clear colorless liquid.

Trans-3-benzyloxy-4-hydroxytetrahydrofuran (0.25 g, 1.3 mmol) obtained from the first step as described above, hexane (3.5 ml), vinyl acetate (0.52 g, 6.08 mmol, 4.6 eq) and Amano II (12.5 mg) were stirred at room temperature. GC analysis after 55 hours showed that the reaction was 50% complete and both the acetate ester produced and the unreacted alcohol had an ee of >98%. After cooling to room temperature the reaction mixture was filtered to remove the enzyme and the filter cake was washed with ethyl acetate (2×5 mL). The volatiles were removed in vacuo to leave a mixture of substantially enantiomerically pure (3S,4S)-trans-3-benzyloxy-4-hydroxytetrahydrofuran and (3R,4R)-trans-3-benzyloxy-4-acetoxytetrahydrofuran which may be separated by the partitioning procedures described hereinabove.

The invention has been described in detail with particular reference to preferred embodiments thereof, but it will be understood that variations and modifications can be effected within the spirit and scope of the invention.

We claim:

1. Process for the preparation of substantially enantiomerically pure (3S,4S)-trans-3-alk(en)yloxy-4-hydroxytetrahydrofuran (Ia) and (3R,4R)-trans-3-alk(en)yloxy-4-acyloxytetrahydrofuran (II) which comprises the steps of:

(1) contacting 3,4-epoxytetrahydrofuran with an alcohol having the formula $R^1$—OH in the presence of an acid catalyst in an inert solvent to obtain a trans-3-alk(en)yloxy-4-hydroxytetrahydrofuran (I) of the formula:

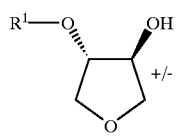

(I)

(2) contacting trans-3-alk(en)yloxy-4-hydroxytetrahydrofuran of formula (I) with a hydrolase enzyme and an acyl donor in the presence of an aprotic solvent to obtain a mixture of a substantially enantiomerically pure (3S,4S)-trans-3-alk(en)yloxy-4-hydroxytetrahydrofuran having formula (Ia) and a substantially enantiomerically pure (3R,4R)-trans-3-alk(en)yloxy-4-acyloxytetrahydrofuran of formula (II):

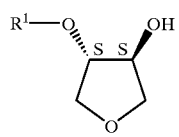

(Ia)

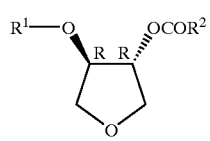

(II)

(3) separating (Ia) and (II) from the mixture obtained in step (2) by partitioning the mixture between water and a water-immiscible solvent to obtain the (3S,4S)-trans-3-alk(en)yloxy-4-hydroxytetrahydrofuran (Ia) in the aqueous phase and the (3R,4R)-trans-3-alk(en)yloxy-4-acyloxytetrahydrofuran (II) in the water-immiscible solvent wherein $R^1$ is an alkyl, alkenyl, arylalkyl or aryl radical and $R^2$ is an alkyl radical.

2. Process according to claim 1 wherein in step (1) the acid catalyst is sulphuric acid, boron trifluoride, an alkali or alkaline earth metal tetrafluoroborate, an alkali or alkaline earth metal trifluoromethanesulphonate or an alkali or alkaline earth metal perchlorate and the inert solvent is a chlorinated hydrocarbon; in step (2) the acyl donor is an alkanoic acid anhydride containing 4 to 10 carbon atoms or an alkyl or alkenyl carboxylate of the general formula

wherein $R^2$ is alkyl containing from 1 to 4 carbon atoms and $R^3$ is alkyl containing from 1 to 6 carbon atoms or alkenyl containing 2 to 4 carbon atoms and the solvent is an ether, a hydrocarbon or an alkyl carboxylate ester and step (2) is carried out at a temperature of about 20 to 80° C.; and in step (3) the water immiscible solvent is an ether, a hydrocarbon or an alkyl carboxylate ester; $R^1$ is $C_1$–$C_8$ alkyl, benzyl or allyl; and $R^2$ is alkyl containing from 1 to 4 carbon atoms.

3. Process according to claim 1 wherein in step (1) the acid catalyst is boron trifluoride and the inert solvent is dichloromethane; in step (2) the alkyl or alkenyl alkanoate is vinyl acetate and the solvent is cyclohexane and step (2) is carried out at a temperature of about 20 to 60° C.; and in step (3) the water immiscible solvent is cyclohexane; R1 is allyl; and $R^2$ is methyl.

4. Process according to claim 1 wherein in step (1) the acid catalyst is magnesium perchlorate and the inert solvent is isobutyronitrile; in step (2) the alkyl or alkenyl alkanoate is vinyl acetate and the solvent is hexane and step (2) is carried out at a temperature of about 20 to 40° C.; and in step (3) the water immiscible solvent is hexane; $R^1$ is benzyl; and $R^2$ is methyl.

5. A substantially enantiomerically pure (3S,4S)-trans-3-alk(en)yloxy-4-hydroxytetrahydrofuran compound having the formula:

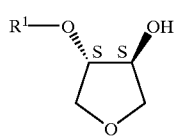

(Ia)

wherein $R^1$ is an alkyl, alkenyl or aryl radical.

6. A compound according to claim 5 wherein $R^1$ is $C_1$–$C_8$ alkyl, or allyl.

7. A substantially enantiomerically pure (3R,4R)-trans-3-alk(en)yloxy-4-acyloxytetrahydrofuran compound having the formula:

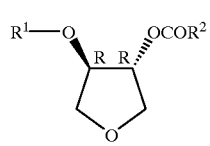

(II)

wherein $R^1$ is an alkyl, alkenyl, arylalkyl or aryl radical and $R^2$ is an alkyl radical.

8. A compound according to claim 7 wherein $R^1$ is $C_1$–$C_8$ alkyl, benzyl or allyl and $R^2$ is alkyl containing from 1 to 4 carbon atoms.

9. A compound according to claim 7 wherein $R^1$ is allyl or benzyl and $R^2$ is methyl.

* * * * *